United States Patent [19]

Davidson et al.

[11] Patent Number: 4,471,116
[45] Date of Patent: Sep. 11, 1984

[54] SUBSTITUTED (10H-PHENOTHIAZIN-10-L)-PROPYL-1-PIPERAZINES

[75] Inventors: Arnold B. Davidson, North Caldwell; Robert W. Guthrie, Saddle Brook; Richard W. Kierstead, North Caldwell; Albert Ziering, Nutley, all of N.J.

[73] Assignee: Hoffmann-La Roche Inc., Nutley, N.J.

[21] Appl. No.: 402,704

[22] Filed: Jul. 28, 1982

[51] Int. Cl.³ .................................. C07D 417/06
[52] U.S. Cl. ............................... 544/43; 544/45; 424/246
[58] Field of Search ................................ 544/43, 45

[56] References Cited
U.S. PATENT DOCUMENTS
3,264,290  8/1966  Bernstein et al. ...................... 544/45

Primary Examiner—Richard Raymond
Attorney, Agent, or Firm—Jon S. Saxe; Bernard S. Leon; William G. Isgro

[57] ABSTRACT

Substituted (10H-phenothiazin-10-yl)propyl-1-piperazines of the formula

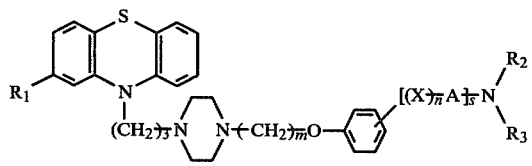

wherein $R_1$, $R_2$, $R_3$, A, X, m, n and s are as hereinafter set forth, are described. The compounds of formula I, which contain a piperazine moiety combined by an ether linkage to different phenolic moieties, are useful as orally active long lasting antipsychotic agents.

15 Claims, No Drawings

SUBSTITUTED (10H-PHENOTHIAZIN-10-L)-PROPYL-1-PIPERAZINES

BRIEF SUMMARY OF THE INVENTION

The invention relates to compounds of the formula

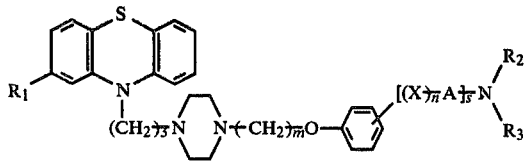

wherein $R_1$ is hydrogen, halogen, trihalomethyl, $-SO_2NR_2R_3$, alkyl, alkylthio or alkoxy, X is oxygen or sulfur, m is 2 to 6, n and s are, independently, zero or 1, A is alkylene and, when X is oxygen, is also 2-hydroxytrimethylene, and $R_2$ and $R_3$, independently, are hydrogen or alkyl, or taken together with the nitrogen atom are a 5-, 6- or 7-membered unsubstituted or substituted heterocyclic ring, when A is 2-hydroxytrimethylene, the respective enantiomers, and acid addition salts thereof with pharmaceutically acceptable acids.

DETAILED DESCRIPTION OF THE INVENTION

As used herein, the term "alkyl" preferably denotes "lower alkyl", which denotes a straight or branched chain saturated hydrocarbon containing 1 to 7 carbon atoms, for example, methyl, ethyl, propyl, isopropyl, butyl, t-butyl, neopentyl, pentyl, heptyl and the like. The term "alkoxy" preferably denotes "lower alkoxy", which denotes an alkyl ether group in which the lower alkyl group is as described above, for example, methoxy, ethoxy, propoxy, butoxy, isobutoxy, pentoxy and the like. The term "alkylthio" preferably denotes "lower alkylthio", which denotes an alkyl thioether group in which the lower alkyl group is as described above, for example, methylthio, ethylthio, propylthio, butylthio, isobutylthio, pentylthio and the like. The term "halogen" or "HAL" denotes all the halogens, i.e., bromine, chlorine, fluorine and iodine. The term "alkylene" preferably denotes a "lower alkylene", which denotes a divalent, straight or branched chain saturated hydrocarbon containing 1 to 7 carbon atoms, for example, methylene, ethylene, trimethylene, tetramethylene, 1,1-dimethylethylene, pentamethylene and the like. The term "5-, 6- or 7-membered unsubstituted or substituted heterocyclic ring" denotes phthalimido, morpholino and the like.

The invention relates to compounds of the formula

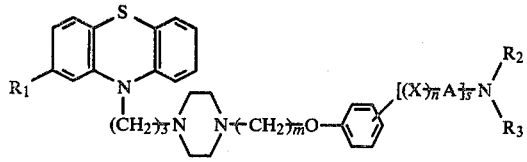

wherein $R_1$ is hydrogen, halogen, trihalomethyl, $-SO_2NR_2R_3$, alkyl, alkylthio or alkoxy, X is oxygen or sulfur, m is 2 to 6, n and s are, independently, zero or 1, A is alkylene and, when X is oxygen, is also 2-hydroxytrimethylene, and $R_2$ and $R_3$, independently, are hydrogen or alkyl, or taken together with the nitrogen atom are a 5-, 6- or 7-membered unsubstituted or substituted heterocyclic ring, when A is 2-hydroxytrimethylene, the respective enantiomers, and acid addition salts thereof with pharmaceutically acceptable acids.

A preferred group of compounds of the inventions comprised compounds of formula I wherein X is oxygen, and n and s each is 1.

A more preferred group of compounds of the invention comprise compounds of formula I wherein $R_2$ and $R_3$, independently, are hydrogen or lower alkyl, and n and s each is zero.

A most preferred group of compounds of the invention comprise compounds of formula I wherein $R_1$ is halogen or trifluoromethyl, X is oxygen, m is 2, n and s each is 1, and $R_2$ and $R_3$, independently, are hydrogen or lower alkyl.

Preferred compounds of formula I are: (S)-1-(1-methylethylamino)-3-[4-[2-[4-[3-(2-chloro-10H-phenothiazin-10-yl)propyl]piperazine-1-yl]ethoxy]phenoxy]-2-propanol; and N-[4-[2-[4-[3-(2-chloro-10H-phenothiazin-10-yl)propyl]-1-piperazinyl]ethoxy]phenyl]-methylethaneamine.

Exemplary of the compounds of formula I are:
(R)-1-(1-methylethylamino)-3-[4-[2-[4-[3-(2-chloro-10H-phenothiazin-10-yl)propyl]piperazin-1-yl]ethoxy]phenoxy]-2-propanol;

(S)-1-(1-methylethylamino)-3-[4-[2-[4-[3-(2-trifluoromethyl)-10H-phenothiazin-10-yl)propyl]piperazin-1-yl]ethoxy]phenoxy]-2-propanol;

1-[3-(2-chloro-10H-phenothiazin-10-yl)propyl]-4-[2-[4-[2-(1-methylethyl)aminoethoxy]phenoxy]ethyl]piperazine trihydrochloride;

1-[3-(2-chloro-10H-phenothiazin-10-yl)propyl]-4-[2-[4-[3-(1-methylethyl)aminopropoxy]phenoxy]ethyl]piperazine;

1-[3-(2-chloro-10H-phenothiazin-10-yl)propyl]-4-[2-[4-[4-(1-methylethyl)aminobutoxy]phenoxy]ethyl]piperazine trihydrochloride;

1-[3-(2-chloro-10H-phenothiazin-10-yl)propyl]-4-[2-[4-[5-(1-methylethyl)aminopentoxy]phenoxy]ethyl]piperazine;

1-[3-(2-methylthio-10H-phenothiazin-10-yl)propyl]-4-[2-[4-[5-(1-methylethyl)aminopentoxy]phenoxy]ethyl]piperazine trimaleate;

1-[3-(2-chloro-10H-phenothiazin-10-yl)-4-[2-[4-[6-(1-methylethyl)aminohexyloxy]phenoxy]ethyl]piperazine trihydrochloride;

(S)-1-(1-methylethylamino)-3-[4-[2-[4-[3-(2-N,N-dimethylsulfamoyl-10H-phenothiazine-10-yl)propyl]piperazine-1-yl]ethoxy]phenoxy]-2-propanol trihydrochloride;

(S)-1-(1-methylethylamino)-3-[4-[2-[4-[3-(2-methoxy-10H-phenothiazin-10-yl)propyl]piperazin-1-yl]ethoxy]phenoxy]-2-propanol trihydrochloride;

(S)-1-(1-methylethylamino)-3-[4-[2-[4-[3-(2-methylthio-10H-phenothiazin-10-yl)propyl]piperazin-1-yl]ethoxy]phenoxy]-2-propanol trihydrochloride;

(S)-1-(1-methylethylamino)-3-[4-[2-[4-[3-(2-methyl-10H-phenothiazin-10-yl)propyl]piperazin-1-yl]ethoxy]phenoxy]-2-propanol trihydrochloride;

3-[[4-[2-[4-[3-(2-chloro-10H-phenothiazin-10-yl)propyl]-1-piperazinyl]ethoxy]phenyl]oxy]-propanamine;

3-[[4-[2-[4-[3-(2-chloro-10H-phenothiazin-10-yl)propyl]-1-piperazinyl]ethoxy]phenyl]oxy]-N-methylpropanamine;

3-[[4-[2-[4-[3-(2-chloro-10H-phenothiazin-10-yl)propyl]-1-piperazinyl]ethoxy]phenyl]oxy]-N,N-dimethylpropanamine trihydrochloride;

N-[4-[2-[4-[3-(2-chloro-10H-phenothiazin-10-yl)-propyl]-1-piperazinyl]ethoxy]phenyl]-alpha-methylethanamine trimaleate;

1-[3-(2-chloro-10H-phenothiazin-10-yl)propyl]-4-[2-[4-[2-(1-methylethyl)aminoethyl]phenoxy]ethyl]piperazine trimaleate;

1-[3-(2-chloro-10H-phenothiazin-10-yl)propyl]-4-[2-[4-[3-(1-methylethyl)aminopropyl]phenoxy]ethyl]piperazine;

1-[3-(2-chloro-10H-phenothiazin-10-yl)propyl]-4-[2-[4-[4-(1-methylethyl)aminobutyl]phenoxy]ethyl]piperazine;

N-[4-[2-[4-[3-(2-trifluoromethyl-10H-phenothiazin-10-yl)propyl]-1-piperazinyl]ethoxy]phenyl]-α-methylethanamine trimaleate;

N-[4-[3-[4-[3-(2-chloro-10H-phenothiazine-10-yl)propyl]-1-piperazinyl]propoxy]phenyl]-α-methanamine trimaleate; and the like.

The compounds of formula I of the invention can be prepared in accordance with Reaction Scheme I which follows:

formula I is converted to an acid addition salt utilizing conventional procedures, as hereinafter further described. The salts produced can be recovered utilizing procedures, such as, crystallization and the like.

The starting materials of the formula

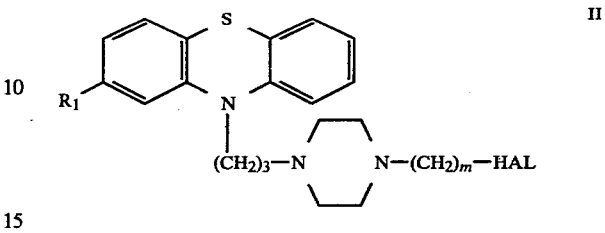

wherein $R_1$ and m are as previously described, and HAL is halogen, are known compounds or can be prepared according to known procedures.

Exemplary of the compounds of formula II are:

1-[3-(2-chloro-10H-phenothiazin-10-yl)propyl]-4-(2-chloroethyl)piperazine;

1-[3-(2-chloro-10H-phenothiazin-10-yl)propyl]-4-(3-chloropropyl)piperazine;

1-[3-(2-trifluoromethyl-10H-phenothiazin-10-yl)propyl]-4-(2-chloroethyl)piperazine;

1-[3-(2-chloro-10H-phenothiazin-10-yl)propyl]-4-(4-chlorobutyl)piperazine;

1-[3-(2-methylthio-10H-phenothiazin-10-yl)propyl]-4-(2-chloroethyl)piperazine; and the like.

The starting materials of the formula

Reaction Scheme I

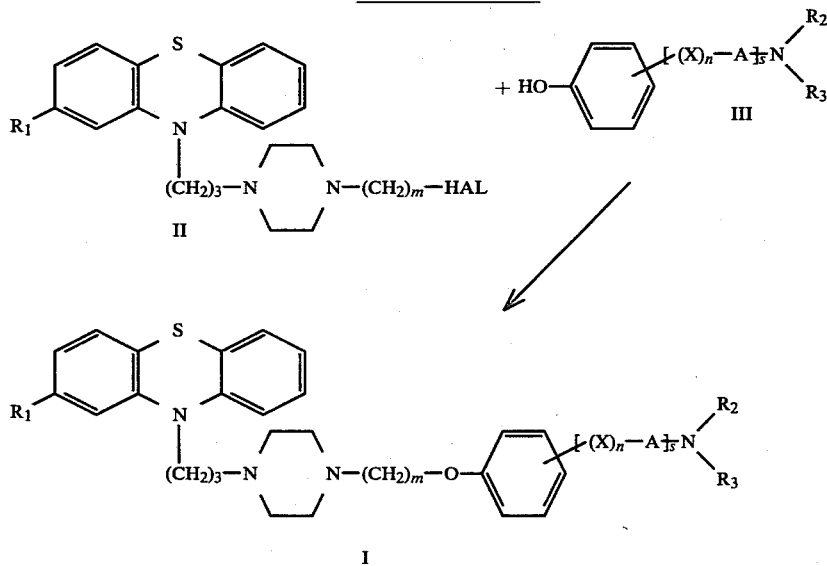

wherein $R_1$, $R_2$, $R_3$, A, X, m, n and s are as previously described.

In Reaction Scheme I, a compound of formula II is reacted with a compound of formula III to yield a compound of formula I in a Williamson ether synthesis utilizing standard conditions. More specifically, the reaction is carried out in the presence of a base, for example, sodium hydroxide, potassium hydroxide, sodium carbonate, potassium carbonate and the like, and a solvent, for example, aqueous dimethylsulfoxide, aqueous dimethylformamide, and the like. Preferably the reaction is carried out at a temperature in the range of from about 20° C. to about 100° C., most preferably at about 50° C.

The resulting compound of formula I can be recovered utilizing conventional extraction procedures, and solvents. More conveniently, the resulting compound of

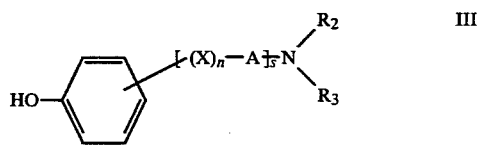

wherein $R_2$, $R_3$, A, X, n and s are as previously described, are known compounds or can be prepared according to known procedures.

Exemplary of the compounds of formula III are:

(a) 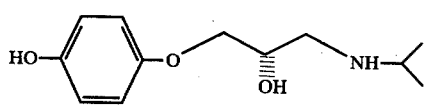

(b) 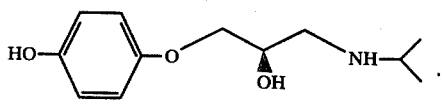

(c) 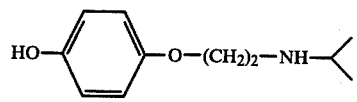

(d) 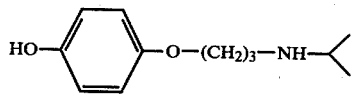

(e) 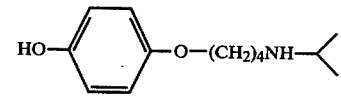

(f) 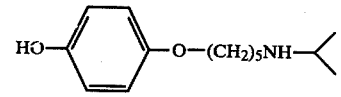

(g) 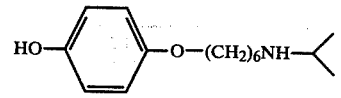

(h) 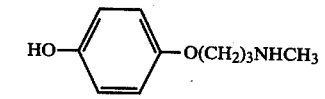

(i) 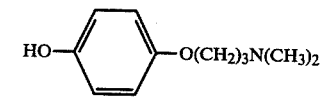

(j) 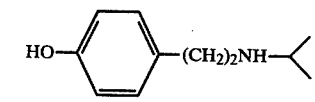

(k) 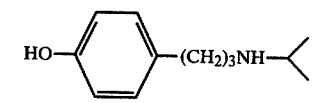

(l) 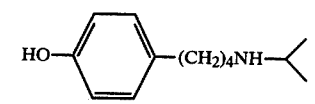

(m) 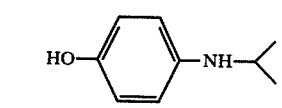

(n) 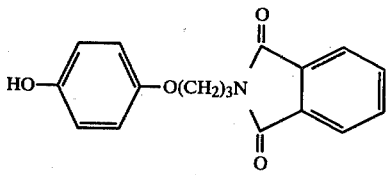

The compounds of formula I form acid addition salts with inorganic or organic acids. Thus, they form pharmaceutically acceptable acid addition salts with both pharmaceutically acceptable organic and inorganic acids, for example, with hydrohalic acid, such as, hydrochloric acid, hydrobromic acid, hydroiodic acid, other mineral acid salts, such as sulfuric acid, nitric acid, phosphoric acid, or the like, alkyl- and mono-aryl sulfonic acids, such as ethanesulfonic acid, toluenesulfonic acid, benzenesulfonic acid, or the like, other organic acids such as acetic acid, tartaric acid, maleic acid, citric acid, benzoic acid, salicyclic acid, ascorbic acid, and the like. Non-pharmaceutically acceptable acid addition salts of compounds of formula I can be converted into pharmaceutically acceptable acid addition salts via conventional metathetic reactions whereby the non-pharmaceutically acceptable anion is replaced by a pharmaceutically acceptable anion; or alternatively, by neutralizing the non-pharmaceutically acceptable acid addition salt and then reacting the so-obtained free base with a reagent yielding a pharmaceutically acceptable acid addition salt.

The compounds of formula I and their pharmaceutically acceptable acid addition salts exhibit neuroleptic activity of long duration. Accordingly, the compounds of formula A are useful as long acting antipsychotic agents, for instance, in the treatment of schizophrenia. The activity of the compounds of formula I which makes them orally useful as antipsychotic agents can be demonstrated in warm-blooded animals, in accordance with known procedures.

For example, by one procedure, trained rats are placed in experimental chambers equipped with a response lever, a steel grid floor for delivery of electric shock and a loudspeaker for presentation of auditory stimuli. Each trial consists of a fifteen-second warning tone (conditioned stimulus), continuing for an additional fifteen seconds accompanied by electric shock (unconditioned stimulus; 1.0 mA, 350 V.A.C., scrambled). The rats can terminate a trial at any point by depression of the response lever. A response during the initial fifteen-second warning tone ends the trial before shock delivery and is considered an avoidance response, while a response occurring during shock delivery is an escape response. Trials are presented every two minutes during a one-hour test session (30 trials per session).

Trained rats maintain a reliable control baseline of avoidance behavior (zero to three avoidance failures per session). Compounds are administered to a minimum of three to four rats at each dose level over a range of doses. Rats receive vehicle alone, during control sessions prior to drug administration. Each rat is tested daily or weekly, after a single drug administration, until avoidance behavior returns to pre-drug baseline levels.

The session is divided into three consecutive twenty minute (ten trial) segments. Response counts are summed over all subjects at a given dose within each segment.

The number of trials in which the rats failed to exhibit an avoidance response (avoidance block) or failed to exhibit an escape response (escape block) is determined for the segment displaying the maximum such effect at each dose. This number is expressed as a percentage of the total trials within the segment. The dose calculated to produce a 50% block of avoidance (ABD 50) is obtained from the dose-effect regression line fitted by the Method of Least Squares. The lowest dose which produced a 20% block of escape responding (EBD 20) is read from a graphic dose-effect plot. In obtaining these values, percent effect is plotted against the log dose.

Antipsychotic agents can be distinguished from other types of drugs, which affect the behavior of rats in this procedure, by the larger separation between doses which block avoidance responding and doses which block escape responding. The clinical potency of antipsychotic drugs with known therapeutic uses and properties is significantly and highly correlated with their potency in this procedure. Consequently, the compounds of formula I may be used therapeutically in dosage ranges consistent with their potency in the test procedure.

When (S)-1-(1-methylethylamino)-3-[4-[2-[4-[3-(2-chloro-10H-phenothiazin-10-yl)propyl]piperazine-1-yl]ethoxy]phenoxy]-2-propanol trihydrochloride (Compound A), which, after a single dose has demonstrated an $LD_{50}$ of, for example, 45 mg/kg, p.o., 7 days, and 77.5 mg/kg, i.p., 24 hours, in mice, is utilized as the test substance, maximum neuroleptic activity is observed 7-10 days after administration at an $ABD_{50}$ of 13.5 mg/kg, p.o.

When N-[4-[2-[4-[3-(2-chloro-10H-phenothiazin-10-yl)propyl]-1-piperazinyl]ethoxy]phenyl]-α-methylethaneamine (Z)-2-butenedioate (Compound B), which, after a single dose, has demonstrated an $LD_{50}$ of, for example, >1000 mg/kg, p.o., 24 hours, 248 mg/kg, p.o., 7 days, and 230 mg/kg, i.p., 7 days, in mice, is utilized as the test substance, maximum neuroleptic activity is observed on the day of administration at an $ABD_{50}$ of 8.7 mg/kg, p.o. (60 minutes pretreatment). In this discrete avoidance procedure, which is highly predictive of antipsychotic activity, the avoidance blocking effect of both compounds was highly specific with little or no escape blocks. The neuroleptic effect of Compound A lasted for several weeks and that of Compound B lasted for several days.

The relative antipsychotic and prolonged duration of activity of the compounds of formula I in the discrete avoidance test are shown in Table I.

The prolonged duration of activity of the Compound A can also be demonstrated in other test procedures sensitive to the effects of neuroleptics. These results are shown in Table 2. The effects of Compound A in several test procedures which are used to predict neuroleptic activity are shown in Table 3.

TABLE 1

| | Discrete Avoidance - Rats | | | | |
|---|---|---|---|---|---|
| | | Percentage Block of Avoidance | | Time of | |
| Compound | Dose mg/kg po | 60 min. post-drug | 24 hrs. post-drug | Peak Effect (AB)* | Duration of Sig. Activity (AB)* |
| (S)—1-(1-methylethylamino)-3-[4-[2-[4-[3-(2-chloro-10H—phenothiazin-10-yl)propyl]piperazine-1-yl]ethoxy]phenoxy]-2-propanol trihydrochloride | 40 | 40% | 77% | 2–10 days (90%) | 8 weeks (30%) |
| 1-[3-(2-chloro-10H—phenothiazin-10-yl)propyl]-4-[2-[4-[2-(1-methylethyl)aminoethoxy]phenoxy]ethyl]piperazine trihydrochloride | 40 | 10% | 100% | 1 day (100%) | 8 weeks (37%) |
| 3-[[4-[2-[4-[3-(2-chloro-10H—phenothiazin-10-yl)-propyl]-1-piperazinyl]ethoxy]phenyl oxy]-N,N—dimethylpropanamine trihydrochloride | 40 | 50% | 100% | 1 day (100%) | >6 weeks (25%) |
| N—[4-[2-[4-[3-(2-chloro-10H—phenothiazin-10-yl)-propyl]-1-piperazinyl]ethoxy]phenyl]-alpha-methylethanamine trimaleate | 30 | 100% | 70% | 60 min. (100%) | 3 days (43%) |
| (S)—1-(1-methylethylamino)-3-[4-[2-[4-[3-(2-trifluoromethyl)-10H—phenothiazin-10-yl)propyl]piperazin-1-yl]ethoxy]phenoxy]-2-propanol trihydrochloride | 25 | 33% | 57% | 3–10 days (77–87%) | 6½ weeks (37%) |
| 3-[[4-[2-[4-[3-(2-chloro-10H—phenothiazin-10-yl)propyl]-1-piperazinyl]ethoxy]phenyl]oxy]propanamine trihydrochloride | 40 | 40% | 73% | 3 days (90%) | 5½ weeks (27%) |
| 1-[3-(2-chloro-10H—phenothiazin-10-yl)propyl]-4-[2-[4-[4-(1-methylethyl)aminobutyl]phenoxy]ethyl]piperazine | 40 | 17% | 100% | 1 day (100%) | 5½ weeks (55%) |
| 1-[3-(2-chloro-10H—phenothiazin-10-yl)propyl]-4-[2-[4-[2-(1-methylethyl)aminoethyl]phenoxy]ethyl]piperazine trimaleate | 40 | 10% | 100% | 1 day (100%) | 5 weeks (80%) |
| 1-[3-(2-chloro-10H—phenothiazin-10-yl)propyl]-4-[2-[4-[3-(1-methylethyl)aminopropyl]phenoxy]ethyl]piperazine trihydrochloride | 40 | 45% | 100% | 1 day (100%) | 5 weeks (55%) |
| 3-[[4-[2-[4-[3-(2-chloro-10H—phenothiazin-10-yl)propyl]-1-piperazinyl]ethoxy]phenyl]oxy]-N—methylpropanamine trihydrochloride | 40 | 65 | 100% | 1 day (100%) | 5 weeks (25%) |
| 1-[3-(2-chloro-10H—phenothiazin-10-yl)propyl]-4-[2-[4-[3-(1-methylethyl)amino-propoxy]phenoxy]ethyl]piperazine trihydrochloride | 40 | 10% | 97% | 1 day (97%) | 5 weeks (50%) |
| 1-[3-(2-chloro-10H—phenothiazin-10-yl)Propyl]-4-[2-[4-[4-(1-methylethyl)aminobutoxy]phenoxy]ethyl]piperazine trihydrochloride | 40 | 20% | 33% | 3–10 days (97–100%) | 5 weeks (30%) |
| (R)—1-(1-methylethylamino-3-[4-[2-[4- | 40 | 20% | 27% | 10 days | 3 weeks |

TABLE 1-continued

| | | Discrete Avoidance - Rats | | | |
|---|---|---|---|---|---|
| | | Percentage Block of Avoidance | | Time of | |
| Compound | Dose mg/kg po | 60 min. post-drug | 24 hrs. post-drug | Peak Effect (AB)* | Duration of Sig. Activity (AB)* |
| [3-(2-chloro-10H—phenothiazin-10-yl)propyl] piperazin-1-yl]ethoxy]phenoxy]-2-propanol trihydrochloride | | | | (37%) | (27%) |
| 1-[3-(2-chloro-10H—phenothiazin-10-yl)propyl]-4-[2-[4-[5-(1-methylethyl)aminopentoxy]phenoxy] ethyl]piperazine trimaleate | 40 | 10% | 97% | 1 day (97%) | 2 weeks (23%) |
| 1-[3-(2-chloro-10H—phenothiazin-10-yl)-4-[2-[4-[6-(1-methylethyl)aminohexyloxy] phenoxy]ethyl]piperazine trihydrochloride | 40 | 23% | 40% | 1 day (40%) | 1 week (30%) |
| 1-[3-(2-methylthio-10H—phenothiazin-10-yl) propyl]-4-[2-[4-[5-(1-methylethyl)aminopentoxy] phenoxy]ethyl]piperazine trimaleate | 40 | 60% | 45% | 60 min. (60%) | 3 days (35%) |

*(AB) = Avoidance block at indicated time.

TABLE 2

| | Effects of Compound A* After A Single Administration | | | | | | | | |
|---|---|---|---|---|---|---|---|---|---|
| Test Procedure | 1-4 hours | 2-4 hours | 1 week | 2 weeks | 3 weeks | 4 weeks | 5 weeks | 6 weeks | 7 weeks | 8 weeks |
| Discrete Avoidance, % Block (Rats, 40 mg/kg, oral) | 40% | 78% | 84% | 80% | 84% | 82% | 56% | 50% | 31% | 30% |
| Pole-Climb Avoidance, % Block (Rats, 40 mg/kg, oral) | 30% | — | 50% | 44% | 11% | — | — | — | — | — |
| Continuous Avoidance, % Decrease of Responding (Rats, 40 mg/kg, oral) | 0% | 59% | 97% | 96% | 93% | 84% | 82% | 55% | 48% | 32% |
| Continuous Avoidance, % Decrease of Responding (Squirrel Monkeys, 5 mg/kg, oral) | 0% | 15% | 35% | 37% | 24% | — | — | — | — | — |
| Apomorphine Induced Emesis % Antagonism (Dogs, 5 mg/kg, subcutaneous) | 93% | 100% | 100% | 100% | 100% | 100% | 100% | 100% | 56% | 40% |
| Serum Prolactin Levels % Increase (Rats, 15 mg/kg, oral) | 215% | 97% | 525% | — | 251% | 56% | — | — | — | — |
| Amphetamine Induced Rotation % Antagonism (S. Nigra Lesioned Rats, 40 mg/kg, oral) | 14% | — | 97% | 95% | 87% | 87% | 62% | 28% | 4% | — |

*Compound A - (S)—1-(1-methylethylamino)-3-[4-[2-[4-[3-(2-chloro-10H—phenothiazin-10-yl)propyl]piperazine-1-yl]ethoxy]phenoxy]-2-propanol trihydrochloride.

TABLE 3

| Test Procedure | Species | Compound A (7 Days Post-Drug) | Haloperidol (1 Hour Post-Drug) | Chlorpromazine (1 Hour Post-Drug) |
|---|---|---|---|---|
| Discrete Avoidance | Rat | | | |
| ABD50 (mg/kg, PO) | | 19 | 0.35 | 5 |
| EBD20/ABD50 Ratio | | >2.1 | 7.8 | 9.6 |
| Continuous Avoidance MED Shocks (mg/kg, PO) | Squirrel Monkey | <5 | 0.28 | 2 |
| Rotation Antagonism ED50 (mg/kg, PO) | Rat | <15 | 0.35 | 20.5 |
| Confinement Motor Activity DD50 (mg/kg, PO) | Rat | 19.6 | 0.4 | 4.6 |
| Anti-Apomorphine Emesis ED50 (mg/kg, SC) | Dog | <5 | 0.02 | 1.4 |
| Inhibition of 3H—Spiroperidol Binding-Caudate IC50 (nM) | Rat (in-vitro) | 1.8 | 6.2 | 11 |
| Dopamine Turnover-Brain Caudate Limbic and Remainder | Rat | 40 mg/kg PO Signif. ↑ Not signif. | 1 mg/kg IP Signif. ↑ Signif. ↑ | 10 mg/kg IP Signif. ↑ Signif. ↑ |
| Dopamine Adenylate Cyclase | Rat | 500 | 250 | 150 |

TABLE 3-continued

| Test Procedure | Species | Compound A (7 Days Post-Drug) | Haloperidol (1 Hour Post-Drug) | Chlorpromazine (1 Hour Post-Drug) |
|---|---|---|---|---|
| Inhibition-Limbic IC50 (nM) | (in-vitro) | | | |
| Prolactin Secretion ID50 (nM) | Rat (in-vitro) | 15 | 27 | 130 |

The compounds of formula I and their pharmaceutically acceptable acid addition salts have antipsychotic effects which, except for duration, are qualitatively similar to those of haloperidol, and chlorpromazine, known for their therapeutic uses and properties. At all concentrations tested, Compound N-[4-[2-[4-[3-(2-chloro-10H-phenothiazin-10-yl)-propyl]-1-piperazinyl]ethoxy]phenyl]-alpha-methylethanamine trimaleate produced no increase in revertant colonies when tested for mutogenicity according to the Ames procedure and it is considered to be free of mutogenic effects. Compound (S)-1-(1-methylethylamino)-3-[4-[2-[4-[3-(2-chloro-10H-phenothiazin-10-yl)propyl]piperazine-1-yl]ethoxy]phenoxy]-2-propanol trihydrochloride increased revertant colonies at the highest concentration tested, however in the absence of data in mammalian test systems, conclusive statements of mutogenic effects in warm-blooded animals cannot be made.

The compounds of formula I and their pharmaceutically acceptable acid addition salts can be used in the form of conventional pharmaceutical preparations. By way of exemplification, suitable oral dosage units comprise or are in the range of from 1 to 500 mg., and suitable oral dosage regimens in warm-blooded animals comprise or are in the range of from about 0.01 mg/kg per day to 50 mg/kg administered at intervals of 3 days to 8 weeks. However, for any particular warm-blooded animal, the specific dosage regimen may be variable and should be adjusted according to individual need and the professional judgment of the person administering or supervising the administration of a compound of formula I or a pharmaceutically acceptable acid addition salt thereof. Furthermore, the frequency with which any such dosage form will be administered will vary, depending upon the quantity of active medicament present therein and the needs and requirements of the pharmacological situation.

For the disclosed use, the compounds of formula I and their pharmaceutically acceptable acid addition salts are formulated, using conventional inert pharmaceutical adjuvant materials, into dosage forms which are suitable for oral or parenteral administration. Such dosage forms include tablets, suspensions, solutions, and the like. Furthermore, the compounds of formula A can be embodied into, and administered in the form of, suitable hard or soft capsules. The identity of the inert adjuvant materials which are used in formulating the compounds of formula I and their pharmaceutically acceptable acid addition salts into oral and parenteral dosage forms will be immediately apparent to persons skilled in the art. These adjuvant materials, either inorganic or organic in nature, include, for example, water, gelatin, lactose, starch, magnesium stearate, talc, vegetable oils, gums, polyalkylene glycols, etc. Moreover, preservatives, stabilizers, wetting agents, emulsifying agents, salts for altering osmotic pressure, buffers, or the like, can be incorporated, if desired, into such formulations.

The compounds of formula I wherein A is 2-hydroxytrimethylene, and their pharmaceutically acceptable acid addition salts possess an asymmetric carbon atom. They are ordinarily obtained as racemic mixtures. The resolution of individual racemates into the optically active isomers, that is, the enantiomers can be carried out by known procedures. Alternatively, optically active isomers can be prepared utilizing, in the processes herein described, corresponding optically active starting materials. Some racemic mixtures can be precipitated as eutectics and can thereafter be separated. Chemical resolution is, however, preferred. By this method, the desired enantiomer is formed from the racemic mixture with an optically active resolving agent, for example, an optically active acid, such as (+)-tartaric acid, (+)-dibenzoyl-D-tartaric acid, (+)-d-10-camphor-sulfonic acid, (−)-3-pinanecarboxylic acid, and the like, to form enantiomeric salt. The formed enantiomers are separated by fractional crystallization and can be converted to the corresponding optical isomer base. Thus, the invention covers the optically active isomers of the compounds of formula I, wherein A is 2-hydroxytrimethylene, as well as their racemates.

The Examples which follow further illustrate the invention. All temperatures are in degrees Centigrade.

EXAMPLE 1

Preparation of 1-[3-(2-chloro-10H-phenothiazin-10-yl)propyl]-4-(2-chloroethyl)piperazine 4-[3-(2-chlorophenothiazin-10-yl)propyl]-1-piperazineethanol (22.5 g) was added to 186 ml of dry dichloromethane containing triethylamine (7.8 ml). The stirred solution was cooled to −10° and maintained at that temperature during the dropwise addition of a solution of 5.1 ml of mesyl chloride in 50 ml of dry dichloromethane. The ice bath was then removed and the reaction was stirred overnight at room temperature. The solution was washed with 25 ml of a 5% sodium bicarbonate solution and then dried over anhydrous potassium carbonate. The solvent was removed in vacuo (bath temperature, 25°) to yield 24.2 g of 1-[3-2-chloro-10H-phenothiazin-10-yl)propyl]-4(2-chloroethyl)piperazine 2a as an oil.

This compound was used as such in subsequent reactions or it could be converted to its dihydrochloride salt and used in that form. Thus in a separate experiment the base 1-[3-(2-chloro-10H-phenthiazin-10-yl)propyl]-4-(2-chloroethyl)piperazine (75 g) in 700 ml of methanol was treated with excess methanlic hydrochloric acid (75 ml; ∼3.5N) and immediately the satl began to crystallize from solution. After stirring for 1 hour at room temperature, the mixture was cooled to 0° and the crystals were removed by filtration, washed with cold methanol and dried in vacuo to constant weight to give 69 g of the di-hydrochloric acid salt of 1-[3-(2-chloro-10H-phenothiazin-10-yl)propyl]-4-(2-chloroethyl)piperazine, mp 147°–149°.

Analysis Calculated for $C_{21}H_{25}Cl_2N_3S \cdot 2HCl$: C, 50.92; H, 5.49; N, 8.48; Cl, 28.63; S, 6.47. Found: C, 51.11; H, 5.48; N, 8.69; Cl, 28.75; S, 6.77.

EXAMPLE 2

Preparation of
1-[3-(2-trifluoromethyl-10H-phenothiazin-10-yl)propyl]-4-(2-chloroethyl)piperazine 4[3-[2-(Trifluoromethyl)phenothiazin-10-yl]propyl]-1-piperazineethanol was converted as described in Example 1 into the chloroethyl compound 1-[3-(2-trifluoromethyl-10H-phenothiazin-10-yl)propyl]-4-(2-chloroethyl)piperazine obtained as an oil.

EXAMPLE 3

Preparation of
1-[3-(2-methylthio-10H-phenothiazine-10-yl)propyl]-4-(2-chloroethyl)piperazine 4-[3-(2-Methylthio-10H-phenothiazin-10-yl)propyl]-1-piperazineethanol was converted as described above in Example 1 to give the corresponding chloro compound 1-[3-(2-methylthio-10H-phenothiazine-10-yl)propyl]-4-(2-chloroethyl)piperazine as an oil. cl EXAMPLE 4

Preparation of
2(S)-3-(1-methylethyl)amino-1,2-propanediol acetonide

Lead tetraacetate (263 g) was dispersed in 1500 ml dry benzene under argon. To the rapidly stirred mixture 140 g of (2R, 3R, 4R, 5R)-mannitol-1,2:5,6-diacetonide was added in 5-10 g portions over 15 minutes and then an additional 1 g portions of the acetonide were added until the reaction gave a negative test for oxidant(potassium iodide-starch paper). A total of 150 g of acetonide (140 g+10×1 g) was used. The mixture was filtered through Celite and the filter cake was washed with 2×100 ml portions of dry benzene. The filtrate was stirred with 300 g anhydrous potassium carbonate for 30 minutes to neutralize acetic acid which was produced in the oxidation. After a second filtration through Celite, the solution of D-glyclraldehyde acetonide thus produced was treated with 450 ml isopropylamine and was hydrogenated over 15 g 10% palladium on carbon (1 atmosphere; 23°). The reaction essentially stopped after the uptake of 26.4 liters of hydrogen. The catalyst was removed by filtration and concentration of the filtrate furnished 188 g of the amine 2(S)-3-(1-methylethyl)amino-1,2-propanediol acetonide. 865 mg of 2(S)-3-(1-methylethyl)amino-1,2-propanediol acetonide in 20 ml ether was cooled to 0° and 4 mmol hydrogen chloride in ether was added. The resulting ppt was collected and washed with ether to give 500 mg of the amine hydrochloride salt, mp 135°-136°; $[\alpha]_D^{25} - 40.5°$ (c, 1.0, $H_2O$).

Analysis Calculated for $C_9H_{18}NO_2 \cdot HCl$: C, 51.55; H, 9.61; N, 6.68; Cl, 16.91. Found: C, 51.56; H, 9.89; N, 7.00; Cl, 16.62.

EXAMPLE 5

Preparation of
(2S)-3-[N-mesyl-(1-methylethyl)amino]-1,2-propanediol acetonide 90 ml mesyl chloride was added with stirring to a previously chilled (−10°) solution of (2S)-3-isopropylamino-1,2-propanediol acetonide (188 g; 1.087 mol) and triethylamine (228 ml; 1.63 mol) in dry tetrahydrofuran at such a rate that the reaction temperature did not exceed 5°. Reaction was then stirred at 10°-15° for 30 minutes whereupon it was diluted with 1.5 L brine. The layers were separated and the aqueous layers were extracted with ether (3×500 ml). The organic layers were washed in turn with brine (2×500 ml) and then were combined, dried over sodium sulfate, and evaporated to give 264 g of (2S)-3-[N-mesyl-(1-methylethyl)amino]-1,2-propanediol acetonide as an oil.

A small portion was recrystallized three times from hexane to give analytically pure material, mp 33°-34°; $[\alpha]_D^{25} - 14.76°$ (c, 1.0, $CHCl_3$).

Analysis Calculated for $C_{10}H_{21}NO_4S$: C, 47.79; H, 8.42; N, 5.57; S, 12.76. Found: C, 47.87; H, 8.66; N, 5.72; S, 12.89.

EXAMPLE 6

Preparation of
(2S)-3-[N-mesyl-(1-methylethyl)amino]-1,2-propanediol 200 ml of prewashed (water and methanol) Dowex 50W-8X ion exchange resin ($H^{30}$ form) was added to a solution of 264 g crude (2S)-3-[N-mesyl-(1-methylethyl)amino]-1,2-propanediol acetonide in methanol (1 liter) and water (325 ml). The mixture was stirred under reflux for 90 minutes. The cooled mixture was filtered and the filtrate was concentrated in vacuo. The residue was evaporated several times from benzene-ethanol mixtures to remove the last traces of water. The resulting solid was triturated with 2.5 L ether to give 159.7 g of (2S)-3-[N-mesyl-(1-methylethyl)amino]-1,2-propanediol, mp 67°-70°. Concentration of the ether furnished an additional 27.7 g of (2S)-3-[N-mesyl-(1-methylethyl)amino]-1,2-propanediol, mp 62°-66°. Crystallization from ethyl acetate-hexane furnished the analytically pure material, mp 73°-74°; $[\alpha]_D^{25} - 15.94°$ (c, 1.0, $H_2O$).

Analysis Calculated for $C_7H_{17}NO_4S$: C, 39.79; H, 8.11; N, 6.63; S, 15.18. Found: C, 39.83; H, 8.40; N, 6,66; S, 14.96.

EXAMPLE 7

Preparation of
(S)-N-(1-methylethyl)-N-(methylsulfonyl)oxiranemethaneamine

A solution of (2S)-3-[N-mesyl-(1-methylethyl)amino]-1,2-propanediol (211.3 g) and benzoic acid (2.5 g) in 180 ml trimethylorthoacetate was heated at 80°-85° in a flask equipped to distill off the methanol as it was formed. After 45 minutes the reaction was cooled and partitioned between dichloromethane (600 ml) and a 5% sodium bicarbonate solution (600 ml). The organic layer was washed with dilute sodium hydroxide solution (2×200 ml) and the aqueous layers were back-washed with dichloromethane (2×200 ml). The combined organic extracts were dried over potassium carbonate and evaporated yielding 265 g of the intermediate orthoacetate as an oil.

The above oil was dissolved in dichloromethane (500 ml) and was treated with 150 ml of chlorotrimethylsilane. The solution was heated at reflux for 45 minutes, then was cooled and concentrated to dryness in vacuo to give 268 g of the chloroacetate.

The above material was dissolved in methanol (400 ml). To this rapidly stirred solution was added water (200 ml) and ice (200 g), followed by a solution of sodium hydroxide (85 g) in water (300 ml) over 2-3 minutes such that the temperature did not exceed 15°. After stirring at 15° for 30 minutes, most of the methanol was removed in vacuo and the mixture was extracted with dichloromethane (2×400 ml). The organic phases were washed with 5% sodium chloride solution (1×200 ml), then were combined, dried and evaporated. The resulting oil was distilled in vacuo to give 182 g of (S)-N-(1-methylethyl)-N-(methylsulfonyl)oxiranemethaneamine (118°/0.1 mm); $[\alpha]_D^{25}$ −20.06° (c, 1.0, methanol).

Analysis Calculated for $C_7H_{15}NO_3S$: C, 43.50; H, 7.82; N, 7.25; S, 16.59. Found: C, 43.26; H, 7.72; N, 7.29; S, 16.65.

EXAMPLE 8

Preparation of (S)-1-(4-benzyloxyphenoxy)-3-[N-mesyl-(1-methylethyl)amino]-2-propanol To a solution of (S)-N-(1-methylethyl)-N-(methylsulfonyl)oxiranemethaneamine (86.98 g) and 4-benzyloxyphenol (100 g) in 100 ml methanol was added potassium t-butoxide (5.04 g) and the mixture was stirred under reflux for 16 hours, whereupon 150 ml 2N sodium hydroxide was added and the reaction turned to a solid mass. It was diluted further with 1 L 1N sodium hydroxide solution and stirred for 1 hour to digest the solids which were then removed by filtration, washed with 1N sodium hydroxide and with water. The still wet crude material was taken up in dichloromethane, and the solution was dried over sodium sulfate and partially evaporated in vacuo to a thick oil (wt 250 g) which was then diluted with stirring using 1 L of ether. The mixture was chilled and the product filtered to give 157.1 g of (S)-1-(4-benzyloxyphenoxy)-3-[N-mesyl-(1-methylethyl)amino]-2-propanol, mp 96°-97°.

Analysis Calculated for $C_{20}H_{27}NO_5S$: C, 61.04; H, 6.91; N, 3.56 Found: C, 61.17; H, 6.90; N, 3.43.

EXAMPLE 9

Preparation of (S)-1-(4-benzyloxyphenoxy)-3-(1-methylethyl)amino-2-propanol

To a stirred slurry of (S)-1-(4-benzyloxyphenoxy)-3-[N-mesyl-(1-methylethyl)amino]-2-propanol (78.7 g) in 300 ml toluene was added isopropenyl methyl ether (29 ml) followed by 0.1 ml phosphorus oxychloride. The reaction mixture was stirred for 2 hours at room temperature to ensure formation of the isopropenyl methyl-ether derivative, whereupon 1 ml of triethylamine was added to neutralize the acid catalyst. The solution was then added dropwise over 30 minutes to a stirred solution of sodium bis-(2-methoxyethoxy) aluminum hydride (70% in benzene; 286 ml) and 300 ml toluene which was maintained at 80° throughout the addition. After stirring for an additional 2 hours at 80°, the reaction was cooled and excess reagent was destroyed by the dropwise addition of 30 ml 2N sodium hydroxide and when the reaction had subsided, 300 ml 2N sodium hydroxide were added. The layers were separated and the organic layer was washed in turn with 1N sodium hydroxide (2×) and with brine (2×). The toluene layer was then diluted with ether (300 ml) and extracted using 800 ml 0.5N hydrochloric acid. The acidic extract was washed with ether and the organic layers were back-washed with 0.5N hydrochloric acid (100 ml). The stirred aqueous extracts were basified using 100 ml 10N sodium hydroxide and the resulting solids were removed by filtration and dried. Crystallization of the crude material from ethyl acetate-hexane furnished 54.7 g of (S)-1-(4-benzyloxyphenoxy)-3-(1-methylethyl)amino-2-propanol, mp 94°-96°.

Analysis Calculated for $C_{19}H_{25}NO_3$: C, 72.35; H, 7.99; N, 4.44 Found: C, 72.38; H, 8.16; N, 4.43.

EXAMPLE 10

Preparation of (2R)-3-mesyloxy-1,2-propanediol acetonide

A solution of 2(S)-glycerol-2,3-acetonide (109 g), obtained from mannitol-1,2:5,6-diacetonide via D-glyceraldehyde acetonide using the method described by LeCocq et al., Biochem., 3, 976 (1964), in 1 L dry dichloromethane was cooled to −35° with stirring. Triethylamine (140 ml) was added followed by the dropwise addition of mesyl chloride (71 ml) over 10 minutes while maintaining the reaction between −35° and −25°. The cooling bath was removed and after 45 minutes, 250 ml 1N hydrochloric acid was added. The layers were separated and the dichloromethane solution was washed in turn with 250 ml portions of water (1×), 1N sodium hydroxide (1×) and water (1×). The aqueous layers were dried over sodium sulfate and evaporated to give 172.1 g of (2R)-3-mesyloxy-1,2-propanediol acetonide as a pale yellow oil.

EXAMPLE 11

Preparation of (2S)-3-(4-benzyloxyphenoxy)-1,2-propanediol acetonide

A solution of sodium hydroxide (39 g) in 200 ml water added to a rapidly stirred solution of (2R)-3-mesyloxy-1,2-propanediol acetonide (172.1 g) and 4-benzyloxyphenol (200 g) in 1.5 L dimethylsulfoxide, and the reaction was heated on a steam bath for 3 hours. The cooled solution was diluted with 1 L 1N sodium hydroxide solution and the resulting solids were washed with dilute sodium hydroxide solution with water. The air-dried solids were taken up in benzene (2 L) and the solution was dried over sodium sulfate, decolorized with charcoal and evaporated in vacuo. The product was dissolved in hot methanol (~1.5 L), cooled to ~40° and filtered free from some non-polar impurity. A small portion of the methanol solution was diluted with water to give (2S)-3-(4-benzyloxyphenoxy)-1,2-propanediol acetonide. Crystallization from hexane furnished the pure specimen, mp 69.5°-71°; $[\alpha]_D^{25}$, +6.26° (c, 1.0, methanol).

Analysis Calculated for $C_{19}H_{22}O_4$: C, 72.59; H, 7.05. Found: C, 72.67; H, 6.90.

EXAMPLE 12

Preparation of (2R)-3-(4-benzyloxyphenoxy)-1,2-propanediol

The methanolic solution of (2S)-3-(4-benzyloxyphenoxy)-1,2-propanediol acetonide (~2 L) from the previous example was diluted with 120 ml water and combined with Dowex 50W-8X ion exchange resin (50 ml) in a flask fitted for distillation. The stirred mixture was heated to boiling and 1.8 L of distillate was collected over 3 hours. The reaction was diluted with ethanol (500 ml) and benzene (500 ml) filtered free of the resin and concentrated to dryness in vacuo. The residue was crystallized from ether and from ethyl acetate to give 137.0 g of (2R)-3-(4-benzyloxyphenoxy)-1,2-propanediol in several crops.

Recrystallization of a sample from ethyl acetate furnished the analytical specimen, mp 125°–126.5°; $[\alpha]_D^{25}$ −5.52° (c, 1.0, methanol).

Analysis Calculated for $C_{16}H_{18}O_4$: C, 70.06; H, 6.61. Found: C, 70.01; H, 6.51.

EXAMPLE 13

Preparation of (2S)-1-chloro-3-(4-benzyloxyphenoxy)-2-propanol

A mixture of (2R)-3-(4-benzyloxyphenoxy)-1,2-propanediol (137 g), trimethylorthoacetate (90 g) and benzoic acid (4 g) stirred and heated at 80° for 45 minutes while distilling methanol from the reaction. The reaction was poured into benzene (750 ml) and the solution was washed with 250 mL 1N sodium hydroxide solution. The aqueous layer was backwashed with benzene and the combined organic extracts were dried over potassium carbonate and evaporated to give 166 g of crude orthoacetate as an oil. The oil was dissolved in dry dichloromethane (500 ml) and treated with chlorotrimethylsilane (135 ml) and refluxed for 30 minutes. The solvent was removed in vacuo to give 170 g of chloroacetate, which was dissolved in 800 ml methanol containing 200 ml 2N methanolic hydrochloric acid. The mixture was left overnight at room temperature and then was concentrated to dryness under reduced pressure and the residue was crystallized from dichloromethane-hexane to give 128.9 g of (2S)-1-chloro-3-(4-benzyloxyphenoxy)-2-propanol. A small amount was recrystallized from ethyl acetate to give the analytical sample, mp 78°–80°; $[\alpha]_D^{25}$ +3.09 (c, 1.0, methanol).

Analysis Calculated for $C_{16}H_{17}O_3Cl$: C, 65.69; H, 5.85; Cl, 12.11. Found: C, 65.43; H, 5.74; Cl, 12.06.

EXAMPLE 14

Preparation of (2R)-1-(4-benzyloxyphenoxy)-3-(1-methylethyl)amino-2-propanol (2S)-1-chloro-3-(4-benzyloxyphenoxy)-2-propanol (14.6 g) and sodium acetate (4.2 g) in 150 ml methanol containing 45 ml isopropylamine was heated at reflux for 16 hours. The solvents were removed in vacuo and the residue was partitioned between benzene (600 ml) and 1N sodium hydroxide (125 ml). The aqueous layer was washed with benzene (200 ml) and the combined organic layers were combined, dried over potassium carbonate and concentrated under reduced pressure to give crude (2R)-1-(4-benzyloxyphenoxy)-3-(1-methylethyl)amino-2-propanol as a crystalline solid. Crystallization from ether afforded 13.7 g of (2R)-1-(4-benzyloxyphenoxy)-3-(1-methylethyl)amino-2-propanol, mp 93°–95°, and recrystallization from ether furnished the analytical material, mp 93.5°–94.5°; $[\alpha]_D^{25}$ +22.1° (c, 1.0, 0.1N hydrochloric acid).

Analysis Calculated for $C_{19}H_{25}NO_3$: C, 72.35; H, 7.99; N, 4.44. Found: C, 72.40; H, 8.02; N, 4.29.

EXAMPLE 15

Preparation of 1-benzyloxy-4-(3-bromopropoxy)benzene

A mixture of 4-benzyloxyphenol (50 g), 1,3-dibromopropane (101 g) and powdered anhydrous potassium carbonate (17.3 g) in acetone (500 ml) was stirred under reflux for 30 hours. The solids were removed by filtration and the filtrate was evaporated to dryness in vacuo. The residue was dissolved in 300 ml of dichloromethane and the resulting solution was washed with 10% sodium hydroxide solution to remove unreacted p-benzyloxyphenol. The dichloromethane extract was dried over potassium carbonate, concentrated in vacuo and distilled giving 33.4 g of 1-benzyloxy-4-(3-bromopropoxy)benzene; bp 180°–195° (0.6 mm) (41% yield, 98% pure by gas chromatography). The structure was confirmed by mass spectrum analysis.

EXAMPLE 16

Preparation of 1-benzyloxy-4-(4-bromobutoxy)benzene

4-Benzyloxyphenol was condensed with 1,4-dibromopropane using essentially the same reaction conditions reported above in Example 15, except that the reaction time was 118 hours and the extraction solvent was toluene. The crude product was crystallized from hexane to afford 1-benzyloxy-4-(4-bromobutoxy)benzene, mp 70°–72°.

Analysis Calculated for $C_{17}H_{19}BrO_2$: C, 60.91; H, 5.71. Found: C, 61.36; H, 5.78.

EXAMPLE 17

Preparation of 1-benzyloxy-4-(5-bromopentoxy)benzene

4-Benzyloxyphenol and 1,5-dibromopentane were reacted under conditions described in Example 15 for 5 days. The crude product isolated by a toluene extraction, was distilled to give 1-benzyloxy-4-(5-bromopentoxy)benzene as an oil (88.9% pure by gas chromatography).

EXAMPLE 18

Preparation of 1-benzyloxy-4-(6-bromohexyloxy)benzene

4-Benzyloxyphenol and 1,6-dibromohexane were reacted using conditions reported in Example 15. The reaction time was 4 days and the extraction solvent used was toluene. The crude product was crystallized from hexane to give 1-benzyloxy-4-(6-bromohexyloxy)benzene, mp 72°–3°.

EXAMPLE 19

Preparation of 1-benzyloxy-4-[3-(1-methylethyl)aminopropoxy]benzene

In a glass lined vessel, 1-benzyloxy-4-(3-bromopropoxy)benzene (33.4 g) in 300 ml of isopropylamine was heated at 100° for 10 hours under nitrogen at 1000 psi, then the excess isopropylamine was removed in vacuo and the residue was dissolved in 300 ml of water. The solution was made alkaline with 10% sodium hydroxide and the resulting oil extracted with dichloromethane. The dichloromethane extract, dried over potassium carbonate, was concentrated and distilled to yield 22.5 g of 1-benzyloxy-4-[3-(1-methylethyl)aminopropoxy]benzene, boiling range 180°–190° (0.5 mm) (97.8% pure by gas chromatography).

EXAMPLE 20

Preparation of 1-benzyloxy-4-[4-(1-methylethyl)aminobutoxy]benzene

As described in Example 19, 1-benzyloxy-4-(4-bromobutoxy)benzene was reacted with isopropylamine at 100° (12 hours; 500 psi) to give 1-benzyloxy-4-[4-(1-methylethyl)aminobutoxyl]benzene. The crude product was not distilled.

EXAMPLE 21

Preparation of
1-benzyloxy-4-[5-(1-methylethyl)aminopentoxy]benzene

As described in Example 19, 1-benzyloxy-4-(5-bromopentoxy)benzene was reacted with isopropylamine at 100° (12 hours; 150 psi) to give 1-benzyloxy-4-[5-(1-methylethyl)aminopentoxy]benzene. The distilled product was 95.2% pure by gas chromatography.

EXAMPLE 22

Preparation of
1-benzyloxy-4-[6-(1-methylethyl)aminohexyloxy]benzene

As described in Example 19, 1-benzyloxy-4-(6-bromohexyloxy)benzene was reacted with isopropylamine at 100° (12 hours; 500 psi) to give 1-benzyloxy-4-[6-(1-methylethyl)aminohexyloxy]benzene. The crude oil was crystallized from pentane yielding the purified product, mp 47°–49°.

EXAMPLE 23

Preparation of
1-benzyloxy-4-(3-methylaminopropoxy)benzene

To 150 ml of ethanol containing methylamine (16 g) was added 1-benzyloxy-4-(3-bromopropyloxy)benzene (14 g). The solution was heated for 12 hours at 100° under nitrogen at 1000 psi. The solvent was evaporated in vacuo and the residue treated with 20% sodium hydroxide to ~pH10. The oil was extracted with ethyl acetate and converted in its hydrochloride salt in the usual manner to give 8.4 g (70%) of 1-benzyloxy-4-(3-methylaminopropoxy)benzene as its hydrochloride salt, mp 202°–204°.

Analysis Calculated for $C_{17}H_{21}NO_2 \cdot HCl$: C, 66.33; N, 7.20; N, 4.55. Found: C, 66.30; H, 7.08; N, 4.60.

EXAMPLE 24

Preparation of
1-benzyloxy-4-(3-dimethylaminopropoxy)benzene

In the manner described above for the preparation of 1-benzyloxy-4-(3-methylaminopropoxy)benzene, 1-benzyloxy-4-(3-bromopropyloxy)benzene was reacted with dimethylamine to give 1-benzyloxy-4-(3-dimethylaminopropoxy)benzene. The product was isolated as its hydrochloride salt and crystallization from isopropanol gave the purified hydrochloride salt of 1-benzyloxy-4-(3-dimethylaminopropoxy)benzene, mp 183°–185°.

EXAMPLE 25

Preparation of
1-benzyloxy-4-(3-phthalimidopropoxy)benzene

A solution of 1-benzyloxy-4-(3-bromopropyloxy)benzene (29.4 g) and potassium phthalimide (20.4 g) in dimethylformamide (150 ml) was stirred and heated on a steam bath for 17 hours under nitrogen. The solvent was distilled in vacuo and water (250 ml) was added to the residue. The mixture was extracted with dichloromethane and the extract dried over anhydrous potassium carbonate. The solvent was evaporated in vacuo and the residue was crystallized from ethanol-acetone to give 10.9 g (31%) of 1-benzyloxy-4-(3-phthalimidopropoxy)benzene, mp 143°–145°. A second crop which was obtained by concentrating the filtrate, weighed 9.2 g (26%), mp 137°–140°. The analysis of a sample, mp 141°–143°, from an earlier run was as follows:

Analysis Calculated for $C_{24}H_{21}NO_4$: C, 74.40; H, 5.46; N, 3.62. Found: C, 74.58; H, 5.58; N, 3.45.

EXAMPLE 26

Preparation of 4-(3-bromopropyl)phenol

To 48% hydrobromic acid solution (110 g) was added 4-(3-hydroxypropyl)phenol (25 g) and heated on a steam bath for 3 hours. After cooling, water (500 ml) was added, the oil was extracted with ether, washed with water and then with dilute sodium bicarbonate solution. The etheral extract was dried over potassium carbonate, evaporated and the residue was distilled in a Kugelrohr apparatus giving 29.6 g (84%) of 4-(3-bromopropyl)phenol, bp 180° (2 mm). The product was 92.6% pure by gas chromatography and mass spectrum was compatible with 4-(3-bromopropyl)phenol.

EXAMPLE 27

Preparation of
4-(4-methoxyphenyl)-N-(1-methylethyl)butylamine

A solution of (50 ml) isopropylamine and 4-(4-methoxyphenyl)butyl bromide (13.7 g) in a glass lined vessel was heated under nitrogen (initial pressure, 500 psi) for 12 hours at 100° C. The solvent was removed in vacuo and water (200 ml) was added to the residue. The solution was acidified with concentrated hydrochloric acid and the solution was extracted with ether. The extract was dried over potassium carbonate and the solvent was removed in vacuo. The residue, 4-(4-methoxyphenyl)-N-(1-methylethyl)butylamine, weighed 9.3 g (75%). The identity and purity (94.8%) of the product was determined by mass spectrum and gas chromatography.

EXAMPLE 28

Preparation of
(S)-1-(4-hydroxyphenoxy)-3-(1-methylethyl)amino-2-propanol

A solution of (S)-1-(4-benzyloxyphenoxy)-3-(1-methylethyl)amino-2-propanol (53.4 g) in 500 ml methanol was hydrogenated over 5 g 10% palladium on carbon (room temperature; 1 atmosphere). Within 40 minutes the uptake of nitrogen stopped abruptly after the absorption of 4,300 ml. The mixture was filtered through Celite and the filtrate was concentrated to dryness under reduced pressure. The resulting colorless solid residue was crystallized from acetone to give 35.2 g of (S)-1-(4-hydroxyphenoxy)-3-(1-methylethyl)amino-2-propanol, mp 127°–129°; $[\alpha]_D^{25} - 20.67°$ (c, 1.0, 0.1N hydrochloric acid).

Analysis Calculated for $C_{12}H_{19}NO_3$: C, 63.98; H, 8.50; N, 6.22. Found: C, 63.81; H, 8.68; N, 6.40.

EXAMPLE 29

Preparation of
(R)-1-(4-hydroxyphenoxy)-3-(1-methylethyl)amino-2-propanol

Hydrogenation of (2R)-1-(4-benzyloxyphenoxy)-3-(1-methylethyl)amino-2-propanol under the conditions reported above for the preparation of (S)-1-(4-hydroxyphenoxy)-3-(1-methylethyl)amino-2-propanol, furnished the dextrorotatory isomer (R)-1-(4-hydroxyphenoxy)-3-(1-methylethyl)amino-2-propanol, mp 126°–127°, $[\alpha]_D^{25} +20.85°$ (c, 1.0, 0.1N hydrochloric acid.

Analysis Calculated for $C_{12}H_{19}NO_3$: C, 63.98; H, 8.50; N, 6.22. Found: C, 64.04; H, 8.53; N, 6.04.

EXAMPLE 30

Preparation of 4-[2-(1-methylethyl)aminoethoxy]phenol 4-(2-Bromoethoxy)phenol (41 g) was added to 300 ml of isopropylamine and the solution was heated for 12 hours at 100° under nitrogen at 250 psi. Excess isopropylamine was removed in vacuo and 300 ml of water added to dissolve the residue. The solution was basified with solid potassium carbonate and the oil extracted with ether. The ether extract was dried over anhydrous potassium carbonate. After the solvent was removed in vacuo and the residue was crystallized from acetone-hexane to yield 21.8 g (59%) of 4-[2-(1-methylethyl)aminoethoxy]phenol, mp 78°–80°.

Analysis Calculated for $C_{11}H_{17}NO_2$: C, 67.66; H, 8.78; N, 7.17. Found: C, 67.57; H, 9.06; N, 7.25.

EXAMPLE 31

Preparation of 4-[3-(1-methylethyl)aminopropoxy]phenol

1-Benzyloxy-4-[3-(1-methylethyl)aminopropoxy]benzene (11.5 g) was added to an hydrogenation bottle containing 250 ml of ethanol and hydrogenated over 1 g of 10% palladium on carbon (room temperature; starting pressure of 50 psi). After the theoretical uptake of hydrogen, the mixture was filtered and the solvent distilled in vacuo giving 8.1 g of 4-[3-(1-methylethyl)aminopropoxy]phenol, mp 92°–100° (96.4% pure by gas chromatography). Mass spectrum was compatible.

EXAMPLE 32

Preparation of 4-[4-(1-methylethyl)aminobutoxy]phenol

1-Benzyloxy-4-[4-(1-methylethyl)aminobutoxy]benzene was debenzylated under the hydrogenating conditions reported above in Example 31. The crude product was crystallized from cyclohexane to give 4-[4-(1-methylethyl)aminobutoxy]phenol, mp 91°–93° (98.6% pure by gas chromatography).

EXAMPLE 33

Preparation of 4-[5-(1-methylethyl)aminopentoxy]phenol

A solution of 1-benzyloxy-4-[5-(1-methylethyl)aminophenoxy]benzene (24 g) in acetic acid (250 ml) was hydrogenated over 1 g 10% palladium on carbon. After shaking for 0.5 hours at room temperature, the theoretical amount of hydrogen was taken up. The solvent was removed by distillation in vacuo and the residue dissolved in water. The solution was basified with saturated sodium bicarbonate solution and the product was recovered by filtration to give 13.0 g (75%) of 4-[5-(1-methylethyl)aminopentoxy]phenol, mp 95°–99° (95.7% pure by gas chromatography). Mass spectrum was compatible with the expected product.

EXAMPLE 34

Preparation of 4-[6-(1-methylethyl)aminohexyloxy]phenol

A solution of the crude 1-benzyloxy-4-(3-dimethylaminopropoxy)benzene was hydrogenated under conditions described above for the preparation of 4-[3-(1-methylethyl)aminoproxy]phenol. A small sample of the crude product, mp 78°–86° was crystallized from cyclohexane to give the analytically pure 4-[6-(1-methylethyl)aminohexyloxy]phenol, mp 90°–92°.

Analysis Calculated for $C_{15}H_{25}NO_2$: C, 71.67; H, 10.03; N, 5.57. Found: C, 71.50; H, 9.93; N, 5.64.

EXAMPLE 35

Preparation of 4-(3-methylaminopropoxy)phenol hydrochloride

A solution of 1-benzyloxy-4-(3-methylaminopropoxy)benzene hydrochloride (8.4 g) in acetic acid (250 ml) was hydrogenated over 0.5 g of 10% palladium on carbon in a Parr apparatus (50°; initial pressure 50 psi). The reaction was completed within 0.4 hours and after the catalyst was removed by filtration, the solvent was distilled in vacuo. The residue was crystallized from methanol-ethyl acetate to give 4.8 g (80% of 4-(3-methylaminopropoxy)phenol hydrochloride, mp 167°–169°.

Analysis Calculated for $C_{10}H_{15}NO_2 \cdot HCl$: C, 55.17; H, 7.41; N, 6.43. Found: C, 54.97; H, 7.42; N, 6.60.

EXAMPLE 36

Preparation of 4-(3-dimethylaminopropoxy)phenol hydrochloride

In the manner described above for the preparation of 4-(3-methylaminopropoxy)phenol hydrochloride, 1-benzyloxy-4-(3-dimethylaminopropoxy)benzene was converted to 4-(3-dimethylaminopropoxy)phenol hydrochloride with the exception that ethanol was used as the reaction solvent. The crude product, after crystallization from ethanol, yielded purified 4-(3-dimethylaminopropoxy)phenol hydrochloride, mp 188°–190°.

EXAMPLE 37

Preparation of 4-[2-(1-methylethyl)aminoethyl]phenol

A mixture of isopropanol (300 ml) and 4-(2-bromoethyl)phenol (17.2 g) in a glass lined vessel was heated at 100° for 12 hours under nitrogen at a starting pressure of 250 psi. The solvent was removed in vacuo and the residue was basified using 10% sodium carbonate solution. The mixture was extracted using ether and the ethereal solution, dried over potassium carbonate, was evaporated in vacuo. The resulting residue crystallized on standing, giving 13.5 g of 4-[2-(1-methylethyl)aminoethyl]phenol, (98% pure by gas chromatography). Mass spectrum was compatible. A small sample was crystallized from cyclohexane-benzene and melted at 102°–104°.

EXAMPLE 38

Preparation of 4-[3-(1-methylethyl)aminopropyl]phenol

Under the conditions outlined above for the preparation of 4-[2-(1-methylethyl)aminoethyl]phenol, 4-(3-bromopropyl)phenol was reacted with isopropylamine. The crude product was distilled in a Kugelrohr apparatus (150°; 1 mm) and the distillate was crystallized from ether to give 4-[3-(1-methylethyl)aminopropyl]phenol (97.9% pure by gas chromatography).

EXAMPLE 39

Preparation of 4-[4-(1-methylethyl)aminobutyl]phenol

4-[4-methoxyphenyl]-N-(1-methylethyl)butylamine (10 g) was added to 48% hydrobromic acid solution (70 ml) and the mixture was refluxed for 3 hours. The residual hydrobromic hydrogen acid was distilled off in vacuo and the residue was made alkaline with 10% sodium carbonate solution. The product was filtered, washed with water and dried to give 5.0 g of 4-[4-(1-methylethyl)aminobutyl]phenol. Mass spectrum and gas chromatography confirmed the identity and purity (93.5%) of the product.

EXAMPLE 40

Preparation of 4-(3-phthalimidopropoxy)phenol

To a hydrogen bottle containing 0.5 g of 10% palladium on carbon and acetic acid (250 ml) was added the above 1-benzyloxy-4-(3-phthalimidopropoxy)benzene (16 g). The mixture was shaken at 50° in the Parr hydrogenation apparatus for about 4 hours and cooled to room temperature. The mixture was filtered and the solvent distilled in vacuo. The residue was crystallized from toluene to yield 10.8 g (88%), mp 135°–7° of 4-(3-phthalimidopropoxy)phenol.

Analysis Calculated for $C_{17}H_{15}NO_4$: C, 68.68; H, 5.09; N, 4.71. Found: C, 68.64; H, 5.22; N, 4.33.

EXAMPLE 41

Preparation of (S)-1-(1-methylethylamino)-3-[4-[2-[4-[3-(2-chloro-10H-phenothiazin-10-yl)propyl]piperazin-1-yl]ethoxy]phenoxy]-2-propanol trihydrochloride.

Method A

To a solution of the chloride of 1-[3-(2-chloro-10H-phenothiazin-10-yl)propyl]-4-(2-chloroethyl)piperazine (9.4 g) in 75 ml dimethylsulfoxide was added (S)-1-(4-hydroxyphenoxy)-3-(1-methylethyl)amino-2-propanol (6.0 g) followed by 6.25 ml 4N sodium hydroxide solution. The mixture was stirred under argon at 55° for 2 hours then was cooled and diluted with 500 ml water and 35 ml 1N sodium hydroxide, and extracted with dichloromethane (3×). The extracts were backwashed with water (2×), dried over potassium carbonate and the solvent was removed in vacuo to give 12.8 g of crude (S)-1-(1-methylethylamino)-3-[4-[2-[4-[3-(2-chloro-10H-phenothiazin-10-yl)propyl]piperazin-1-yl]ethoxy]phenoxy]-2-propanol as an oil.

The oil was dissolved in methanol and treated with an excess of methanolic hydrogen chloride (~6N; 12 ml). The solution was concentrated by boiling to 70 ml then it was cooled and 70 ml of ether was added to the cloud point. The mixture was cooled and the resulting solid was filtered to give 13.4 g of the trihydrochloride of (S)-1-(1-methylethylamino)-3-[4-[2-[4-[3-(2-chloro-10H-phenothiazin-10-yl)propyl]piperazin-1-yl]ethoxy]phenoxy]-2-propanol, mp 245°–248°.

The material was recrystallized from methanol-ethyl acetate to give 11.0 g of (S)-1-(1-methylethylamino)-3-[4-[2-[4-[3-(2-chloro-10H-phenothiazin-10-yl)propyl]-piperazin-1-yl]ethoxy]phenoxy]-2-propanol trihydrochloride, 247°–249°.

Method B

To a mixture of the dihydrochloride salt of 1-[3-(2-chloro-10H-phenothiazin-10-yl)propyl]-4-(2-chloroethyl)piperazine (12.4 g) and (S)-1-(4-hydroxyphenoxy)-3-(1-methylethyl)amino-2-propanol (6.2 g) in 100 ml dimethylsulfoxide was added 15.25 ml of 5N sodium hydroxide solution and the mixture was stirred under argon for 2 hours at 50°. The reaction was worked up as in method A to give 14.7 g of the crude (S)-1-(1-methylethylamino)-3-[4-[2-[4-[3-(2-chloro-10H-phenothiazin-10-yl)propyl]piperazin-1-yl]ethoxy]phenoxy]-2-propanol.

The product was converted to its trihydrochloride salt as before yielding 15.5 g of crude salt. Two crystallizations from methanol-ethyl acetate furnished 11.2 g of the trihydrochloride salt of (S)-1-(1-methylethylamino)-3-[4-[2-[4-[3-(2-chloro-10H-phenothiazin-10-yl)propyl]piperazin-1-yl]ethoxy]phenoxy]-2-propanol, mp 251°–253°; $[\alpha]_D^{25} -9.82°$ (c, 1.0, methanol).

Analysis Calculated for $C_{33}H_{43}ClN_4O_3S.3$ HCl: C, 55.00; H, 6.43; N, 7.77; Cl, 19.68; S, 4.44. Found: C, 54.66; H, 6.44; N, 7.75; Cl, 19.60; S, 4.28.

EXAMPLE 42

Preparation of (R)-1-(1-methylethylamino)-3-[4-[2-[4-[3-(2-chloro-10H-phenothiazin-10-yl)propyl]piperazin-1-yl]ethoxy]phenoxy]-2-propanol, trihydrochloride Using the conditions outlined in method A, 11.7 g of 1-[3-(2-chloro-10H-phenothiazin-10-yl)propyl]-4-(2-chloroethyl)piperazine was reacted with 7.5 g of (R)-1-(4-hydroxyphenoxy)-3-(1-methylethyl)amino-2-propanol to give, after recrystallization from methanol-ethyl acetate and from methanol-ethanol, the trihydrochloride salt of (S)-1-(1-methylethylamino)-3-[4-[2-[4-[3-(2-chloro-10H-phenothiazin-10-yl)propyl]piperazin-1-yl]ethoxy]phenoxy]-2-propanol, trihydrochloride, mp 251.5°–253°; $[\alpha]_D^{25} +10.37°$ (c, 1.0, methanol).

Analysis Calculated for $C_{33}H_{43}ClN_4O_3S.3HCl$: C, 55.00; H, 6.43; N, 7.77; Cl, 19.68; S, 4.44. Found: C, 55.18; H, 6.50; N, 7.69; Cl, 19.35; S, 4.50.

EXAMPLE 43

Preparation of (S)-1-(1-methylethylamino)-3-[4-[2-[4-[3-(2-trifluoromethyl)-10H-phenothiazin-10-yl)propyl]piperazin-1-yl]ethoxy]phenoxy]-2-propanol trihydrochloride 1-[3-(2-Trifluoromethyl)-10H-phenothiazin-10-yl)propyl]-4-(2-chloroethyl)piperazine (4.8 g) and (S)-1-(4-hydroxyphenoxy)-3-(1-methylethyl)amino-2-propanol (2.84 g) in 100 ml dimethylsulfoxide were heated with 2.9 ml 4N sodium hydroxide solution and maintained at 55° for 1 hour. The usual work up afforded 6.4 g of crude free base.

6.0 g of the product was converted to its trihydrochloride using methanolic hydrogen chloride and the salt was recrystallized (2×) from methanol-ethyl acetate to give 4.03 g of (S)-1-(1-methylethylamino)-3-[4-[2-[4-[3-(2-trifluoromethyl)-10H-phenothiazin-10-yl)propyl]-piperazine-1-yl]ethoxy]phenoxy]-2-propanol trihydrochloride, mp 242°–244°; $[\alpha] -7.59°$ (c, 1.0, methanol).

Analysis Calculated for $C_{34}H_{43}F_3N_4O_3S.HCl$: C, 54.15; H, 6.15; N, 7.43; F, 7.56; Cl, 14.10; S, 4.25. Found: C, 53.96; N, 6.17; N, 7.28; F, 7.31; Cl, 14.06; S, 4.38.

EXAMPLE 44

Preparation of 1-[3-(2-chloro-10H-phenothiazin-10-yl)propyl]-4-[2-[4-2-(1-methylethyl)aminoethoxy]phenoxy]ethyl]piperazine trihydrochloride Using the conditions essentially described in method A above, 1-[3-(2-chloro-10H-phenothiazin-10-yl)propyl]-4-(2-chloroethyl)piperazine (10.6 g) was reacted with 4-[2-(1-methylethyl)aminoethoxy]phenol (4.88) in dimethylsulfoxide (125 ml) containing sodium hydroxide (1.0 g) in water (7 ml). The crude free base was extracted using ethyl acetate and the dried extract was treated with excess hydrogen chloride in ethyl acetate to furnish the crude trihydrochloride salt. Crystallization of the crude from methanol-isopropanol afforded 2.5 g of 1-[3-(2-chloro-10H-phenothiazin-10-yl)propyl]-4-[2-[4-[2-(1-methylethyl)aminoethoxy]phenoxy]ethyl]piperazine trihydrochloride, mp 223°–235°.

Analysis Calculated for $C_{32}H_{41}ClN_4O_2S.3HCl$: C, 55.65; H, 6.42; N, 8.11 Found: C, 55.61; H, 6.56; N, 7.97.

EXAMPLE 45

Preparation of 1-[3-(2-chloro-10H-phenothiazin-10-yl)propyl]-4-2-[4-[3-(1-methylethyl)aminopropoxy]phenoxy]ethyl]piperazine trihydrochloride Using the conditions described above in method A, 1-[3-(2-chloro-10H-phenothiazin-10-yl)propyl]-4-(2-chloroethyl)piperazine (13.9 g) and 4-[3-(1-methylethyl)aminopropyl]phenol (7.0 g) were reacted in the presence of 9.25 ml 4.0N sodium hydroxide in 100 ml dimethylsulfoxide. The crude free base, isolated by extraction using chloroform, was dissolved in ethyl acetate and treated with hydrogen chloride in ethyl acetate to give the crude trihydrochloride salt. Crystallization from methanol-isopropanol yielded 10.8 g of 1-[3-(2-chloro-10H-phenothiazin-10-yl)propyl]-4-[2-[4-[3-(1-methylethyl)aminopropyl]phenoxy]ethyl]piperazine trihydrochloride, mp 215°–225°.

Analysis Calculated for $C_{33}H_{43}ClN_4O_2S.3HCl$: C, 56.25; H, 6.58; N, 7.95. Found: C, 56.59; H, 6.48; N, 7.78.

EXAMPLE 46

Preparation of 1-[3-(2-chloro-10H-phenothiazin-10-yl)propyl]-4-[2-[4-[4-(1-methylethyl)aminobutoxy]phenoxy]ethyl]piperazine trihydrochloride A solution of 1-[3-(2-chloro-10H-phenothiazin-10-yl)propyl]-4-(2-chloroethyl)piperazine (3.8 g) and 4-[4-(1-methylethyl)aminobutoxy]phenol (2.0 g), in 100 ml dimethylsulfoxide was reacted with sodium hydroxide (0.4 g) in 3 ml water under the conditions described in method A. The crude amine, extracted into ethyl acetate, was converted to the trihydrochloride salt by addition of excess hydrogen chloride in ethyl acetate to the dried extract. The crude salt was triturated with a small amount of hot methanol, then was crystallized from methanol-ethyl acetate to give 2.0 g of 1-[3-(2-chloro-10H-phenothiazin-10-yl)propyl]-4-[2-[4-[4-(1-methylethyl)aminobutoxy]phenoxy]ethyl]piperazine trihydrochloride, mp 220°–221°.

Analysis Calculated for $C_{34}H_{45}ClN_4O_2S.3HCl$: C, 56.82; H, 6.73; N, 7.80. Found: C, 56.95; H, 6.59; N, 7.78.

EXAMPLE 47

Preparation of 1-[3-(2-chloro-10H-phenothiazin-10-yl)propyl]-4-[2-[4-[5-(1-methylethyl)aminopentoxy]phenoxy]ethyl]piperazine trihydrochloride A solution of 1-[3-(2-chloro-10H-phenothiazin-10-yl)propyl]-4-(2-chloroethyl)piperazine (9.2 g) and 4-[5-(1-methylethyl)aminopentoxy]phenol (5.16 g) in 150 ml dimethylsulfoxide was treated with sodium hydroxide (0.87 g) in water (7 ml) and was stirred at 55°–60° for 5 hours. The usual work-up furnished the crude trihydrochloride salt which was recrystallized from methanol to give 5.8 g of 1-[3-(2-chloro-10H-phenothiazin-10-yl)propyl]-4-[2-[4-[5-(1-methylethyl)aminopentoxy]phenoxy]ethyl]piperazine trihydrochloride, mp 237°–239°.

Analysis Calculated for $C_{35}H_{47}ClN_4O_2S.3HCl$: C, 57.38; H, 6.88; N, 7.65. Found: C, 57.09; H, 6.98; N, 7.50.

EXAMPLE 48

Preparation of 1-[3-(2-methylthio-10H-phenothiazin-10-yl)propyl]-4-[2-[4-[5-(1-methylethyl)aminopentoxy]phenoxy]ethyl]piperazine trimaleate A solution of 1-[3-(2-methylthio-10H-phenothiazin-10-yl)propyl]-4-(2-chloroethyl)piperazine (3.2 g) and 4-[5-(1-methylethyl)aminopentoxy]phenol (2.0 g) in 50 ml dimethylsulfoxide was treated with a solution of sodium hydroxide (0.3 g) in water (2 ml). The mixture was stirred for 5 hours at 55°–60° and then was worked up in the usual manner. The product was isolated as its trimaleate salt which was purified by crystallization from methanol-ethyl acetate to yield 1-[3-(2-methylthio-10H-phenothiazin-10-yl)propyl]-4-[2-[4-[5-(1-methylethyl)aminopentoxy]phenoxy]ethyl]piperazine trimaleate, mp 136°–138°.

Analysis Calculated for $C_{36}H_{50}N_4O_2S_2.3C_4H_4O_4$: C, 58.64; H, 6.36; N, 5.70; S, 6.52. Found: C, 58.60; H, 6.51; N, 5.83; S, 6.23.

EXAMPLE 49

Preparation of 1-[3-(2-chloro-10H-phenothiazin-10-yl)]-4-[2-[4-[6-(1-methylethyl)aminohexyloxy]phenoxy]ethyl]piperazine trihydrochloride A solution of 1-[3-(2-chloro-10H-phenothiazin-10-yl)propyl]-4-(2-chloroethyl)piperazine (10.8 g) and 4-[6-(1-methylethyl)aminohexyloxy]phenol (6.3 g) in 125 ml dimethylsulfoxide was treated with sodium hydroxide (1.0 g) in 7 ml water. The reaction was run as before (1 hour; 55°) and worked up in the usual manner ethyl acetate extraction and precipitation of the salt using hydrogen chloride in ethyl acetate. The crude trihydrochloride salt was crystallized from methanol to give 5.1 g of 1-[3-(2-chloro-10H-phenothiazin-10-yl)]-4-[2-[4-[6-(1-methylethyl)aminohexyloxy]phenoxy]ethyl]piperazine trihydrochloride, mp 199°–203°.

Analysis Calculated for $C_{36}H_{49}ClN_4O_2S.3HCl$: C, 57.91; H, 7.02; N, 7.50. Found: C, 57.99; H, 7.15; N, 7.23.

EXAMPLE 50

Preparation of 3-[[4-[2-[4-[3-(2-chloro-10H-phenothiazin-10-yl)propyl]-1-piperazinyl]ethoxy]phenyl]oxy]propanamine trihydrochloride To a stirred solution of 1-[3-(2-chloro-10H-phenothiazin-10-yl)propyl]-4-(2-chloroethyl) piperazine (24 g) and 14.5 g of 4-(3-phthalimidopropyloxy)phenol in dimethylsulfoxide (500 ml) at 50° under nitrogen was added sodium hydroxide (1.9 g) in water (15 ml), and the solution was stirred for 5 hours 55°–60°. After standing at room temperature overnight, the reaction was poured into water (1 L) and the oil was extracted using ethyl acetate. The extract dried over sodium sulfate was evaporated in vacuo and the residual material was dissolved in acetonitrile. The supernatant was decanted from some insoluble material and then hydrogen chloride was bubbled into the solution to precipitate the product as the dihydrochloride salt. Methanol was added to the mixture to redissolve the salt and the solution was concentrated until a solid started to precipitate. The solid was collected by filtration to give 2 g of 1-[3-(2-chloro-10H-phenothiazin-10-yl)propyl]-4-[2-[4-(3-phthalimidopropyloxy)phenoxy]ethyl]piperazine as its di-hydrochloride salt, mp 233°–246°. The filtrate was evaporated and the resulting oil was crystallized from methanol yielding an additional 8.3 g of the same material, mp 225°–240°

To 500 ml of ethanol containing 1-[3-(2-chloro-10H-phenothiazin-10-yl)propyl]-4-[2-[4-(3-phthalimidopropyloxy)phenoxy]ethyl]piperazine (10.5 g) was added 85% hydrazine hydrate (2.95 g). The solution was stirred and refluxed for 24 hours. The insoluble phthalazinedione was then removed by filtration and the filtrate concentrated in vacuo. Water (200 ml) and concentrated ammonium hydroxide (50 ml) was added to the residue. The oil was extracted with dichloromethane and the solution dried over anhydrous sodium sulfate. The solvent was removed in vacuo and the residue dissolved in ethyl acetate. Hydrogen chloride was bubbled into the solution to precipitate the product as its trihydrochloride salt which was recovered by filtration and crystallized from acetonitrile-methanol. The yield of 3-[[4-[2-[4-[3-(2-chloro-10H-phenothiazin-10-yl)propyl]-1-piperazinyl]ethoxy]phenyl]oxy]-propanamine trihydrochloride, mp 237°–240°, was 6.0 g.

Analysis Calculated for $C_{30}H_{37}ClN_4O_2S \cdot 3HCl$: C, 54.39; H, 6.09; N, 8.46. Found: C, 54.06; H, 6.03; N, 8.18.

EXAMPLE 51

Preparation of 3-[[4-[2-[4-[3-(2-chloro-10H-phenothiazin-10-yl)propyl]-1-piperazinyl]ethoxy]phenyl]oxy]-N-methylpropanamine trihydrochloride A solution of 4-(3-methylaminopropoxy)phenol hydrochloride (4.7 g) and 1-[3-(2-chloro-10H-phenothiazin-10-yl)propyl]-4-(2-chloroethyl)piperazine (10.7 g) (as its dihydrochloride) in dimethylsulfoxide (125 ml) was stirred under nitrogen during the addition of sodium hydroxide (3.46 g) in water (5 ml). The reaction was then stirred at 55° for 4 hours and then was diluted with water (500 ml). The oil which separated was extracted into ethyl acetate and hydrogen chloride was bubbled into the solution previously dried over potassium carbonate to precipitate the crude product as its trihydrochloride salt (4.3 g). Crystallization of the salt from acetonitrile-methanol yielded 1.9 g of 3-[[4-[2-[4-[3-(2-chloro-10H-phenothiazin-10-yl)propyl]-1-piperazinyl]ethoxy]phenyl]oxy]-N-methylpropanamine trihydrochloride, mp 223°–226°.

Analysis Calculated for $C_{31}H_{39}ClN_4O_2S \cdot 3HCl$: C, 55.03; H, 6.26; N, 8.28. Found: C, 54.96; H, 6.27; N, 8.23.

EXAMPLE 52

Preparation of 3-[[4-[2-[4-[3-(2-chloro-10H-phenothiazin-10-yl)propyl]-1-piperazinyl]ethoxy]phenyl]oxy]-N,N-dimethylpropanamine trihydrochloride A solution of 1-[3-(2-chloro-10H-phenothiazin-10-yl)propyl]-4-(2-chloroethyl)piperazine (4.22 g) and 4-(3-dimethylaminopropoxy)phenol hydrochloride, (2.3 g) in dimethylsulfoxide (100 ml) was stirred under nitrogen and warmed to 55° C. Then a solution of sodium hydroxide (0.8 g) in water (3 ml) was added and the reaction was stirred at 55°–65° for 2 hours. The usual work-up furnished the crude salt, which was crystallized from methanol-ethyl acetate to give 1.5 g of 3-[[4-[2-[4-[3-(2-chloro-10H-phenothiazin-10-yl)propyl]-1-piperazinyl]ethoxy]phenyl]oxy]-N,N-dimethylpropanamine trihydrochloride, mp 228°–230°.

EXAMPLE 53

Preparation of N-[4-[2-[4-[3-(2-chloro-10H-phenothiazin-10-yl)propyl]-1-piperazinyl]ethoxy]phenyl]-alpha-methylethanamine trimaleate A mixture of 1-[3-(2-chloro-10H-phenothiazin-10-yl)propyl]-4-(2-chloroethyl) piperazine dihydrochloride (52.0 g) and 4-isopropylaminophenol (16.65 g) in dimethylsulfoxide (500 ml) was treated with an aqueous solution of sodium hydroxide (4.0N; 79.5 ml) and the reaction was stirred under an atmosphere of argon 55° for 3 hours. The cooled mixture was diluted with water (0.1.5 L) and extracted (2×) with toluene. The extracts dried over potassium carbonate were decolorized using charcoal, and then evaporated under reduced pressure. The residual oil was dissolved in ethyl acetate (1.2 L). The resulting solution was treated with a solution of maleic acid (38 g) in methanol (300 ml). The precipitated crude trimalate salt was removed by filtration and recrystallized (2×) from methanol to yield 43.2 g of N-[4-[2-[4-[3-(2-chloro-10H-phenothiazin-10-yl)propyl]-1-piperazinyl]ethoxy]phenyl]-alpha-methylethanamine trimaleate, mp 183°–185°.

Analysis Calculated for $C_{30}H_{37}ClN_4OS \cdot 3C_4H_4O_4$: C, 56.98; H, 5.58; N, 6.33. Found: C, 57.13; H, 5.64; N, 6.14.

EXAMPLE 54

Preparation of 1-[3-(2-chloro-10H-phenothiazin-10-yl)propyl]-4-[2-[4-[2-(1-methylethyl)aminoethyl]phenoxy]ethyl]piperazine trimaleate A solution of 1-[3-(2-chloro-10H-phenothiazin-10-yl)propyl]-4-(2-chloroethyl)piperazine (10 g) and 4-[2-(1-methylethyl)aminoethyl]phenol (4.22 g) in dimethylsulfoxide (100 ml) was stirred under nitrogen and warmed to 50° C. A solution of sodium hydroxide (1 g) in water (7 ml) was added. The resulting solution was heated at 55°–60° for 5 hours. To the cooled reaction mixture was added water (200 ml) and the oil extracted with dichloromethane. The solution, dried over potassium carbonate, was evaporated in vacuo and the residue was converted to the trihydrochloride salt. The crude salt was crystallized from methanol-ethyl acetate to afford 3.9 g of product, mp 244°–246°. This salt was dissolved in water and converted to the base by the addition of potassium carbonate. The oil was extracted with ethyl acetate and the solution dried as above. The solvent was distilled in vacuo to yield 3 g of the free base. A solution of the crude 4-[6-(1-methylethyl)aminohexyloxy]phenol in ethanol (10 ml) was added to a solution of maleic acid (1.85 g) in ethanol (10 ml). The resulting crystalline solid was filtered to give 4 g of 1-[3-(2-chloro-10H-phenothiazin-10-yl)propyl]-4-[2-[4-[2-(1-methylethyl)aminoethyl]phenoxy]ethyl]piperazine trimaleate, mp 178°–180°.

Analysis Calculated for $C_{32}H_{41}ClN_4OS \cdot 3C_4H_4O_4$: C, 57.86; H, 5.85; N, 6.13. Found: C, 58.05; H, 5.91; N, 5.94.

EXAMPLE 55

Preparation of 1-[3-(2-chloro-10H-phenothiazin-10yl)propyl]-4-[2-[4-[3-(1-methylethyl)aminopropyl]phenoxy]ethyl]piperazine trihydrochloride A stirred solution of 1-[3-(2-chloro-10H-phenothiazin-10-yl)propyl]-4-(2-chloroethyl) piperazine (10 g) and 4-[3-(1-methylethyl)aminopropyl]phenol (4.5 g) in 100 ml dimethylsulfoxide containing sodium hydroxide (0.94 g) in water (7 ml) was stirred at 55°-60° for 5 hours. The crude trihydrochloride salt obtained after the usual work-up was crystallized from methanol-acetonitrile to yield 4.5 g of 1-[3-(2-chloro-10H-phenothiazin-10-yl)propyl]-4-[2-[4-[3-(1-methylethyl)aminopropyl]phenoxy]ethyl]piperazine trihydrochloride, mp 216°-218°.

Analysis Calculated for $C_{33}H_{43}ClN_4OS \cdot 3HCl$: C, 57.56; H, 6.73; N, 8.14. Found: C, 57.25; H, 6.94; N, 7.93.

EXAMPLE 56

Preparation of 1-[3-(2-chloro-10H-phenothiazin-10-yl)propyl]-4-[2-[4-[4-(1-methylethyl)aminobutyl]phenoxy]ethyl]piperazine trihydrochloride A solution of 1-[3-(2-chloro-10H-phenothiazin-10-yl)propyl]-4-(2-chloroethyl)piperazine (10 g) and 4-[4-(1-methylethyl)aminobutyl]phenol (4.9 g) was stirred at 55° under nitrogen and a solution of sodium hydroxide (0.94 g) in water (7 ml) was added. The reaction was stirred and heated at 55°-65° for 5 hours. The usual work-up yielded the crude trihydrochloride salt. Crystallization of the product from methanol-ethanol yielded 5.3 g of 1-[3-(2-chloro-10H-phenothiazin-10-yl)propyl]-4-[2-[4-[4-(1-methylethyl)aminobutyl]phenoxy]ethyl]piperazine trihydrochloride, mp 245°-248°.

Analysis Calculated for $C_{34}H_{45}ClN_4OS \cdot 3HCl$: C, 58.12; H, 6.89; N, 7.97. Found: C, 57.88; H, 6.83; N, 7.85.

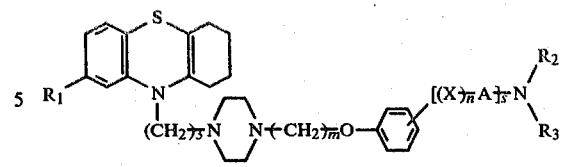

wherein $R_1$ is hydrogen, halogen, trihalomethyl, $-SO_2NR_2R_3$, alkyl, alkylthio or alkoxy, X is oxygen or sulfur, m is 2 to 6, n and s are, independently, zero or 1, A is alkylene and, when X is oxygen, is also 2-hydroxytrimethylene and $R_2$ and $R_3$, independently, are hydrogen or alkyl, or taken together with the nitrogen atom are a 5-, 6- or 7-membered unsubstituted or substituted heterocyclic ring, when A is 2-hydroxytrimethylene, an enantiomer thereof, or an acid addition salt thereof with a pharmaceutically acceptable acid.

2. A compound in accordance with claim 1, wherein $R_2$ and $R_3$, independently, are hydrogen or lower alkyl.

3. A compound in accordance with claim 2, wherein X is sulfur.

4. A compound in accordance with claim 2, wherein X is oxygen.

5. A compound in accordance with claim 4, wherein $R_1$ is halogen or trifluoromethyl, m is 2, and n and s each is 1.

6. A compound in accordance with claim 2, wherein $R_1$ is halogen or trifluoromethyl, m is 2, and n and s each is zero.

7. A compound in accordance with claim 1, wherein $R_2$ and $R_3$ taken together with the nitrogen atom are a 5-,6- or 7-membered unsubstituted or substituted heterocyclic ring.

8. A compound in accordance with claim 7, wherein X is sulfur.

9. A compound in accordance with claim 7, wherein X is oxygen.

10. A compound in accordance with claim 9, wherein

EXAMPLE 57

| | CAPSULE FORMULATIONS | | | | | | | |
|---|---|---|---|---|---|---|---|---|
| Item Ingredients | 1 mg | 5 mg | 15 mg | 30 mg | 60 mg | 100 mg | 250 mg | 500 mg |
| 1. (S)—1-(1-Methylethylamino)-3-[4-[2-[4-[3-(2-chloro-10H—phenothiazin-10-yl)propyl]piperazine-1-yl]ethoxy]phenoxy]-2-propanol trihydrochloride | 1 | 5 | 15 | 30 | 60 | 100 | 250 | 500 |
| 2. Lactose | 203 | 199 | 239 | 224 | 194 | 99 | 148 | — |
| 3. Starch | 30 | 30 | 30 | 30 | 30 | 30 | 30 | 45 |
| 4. Talc | 15 | 15 | 15 | 15 | 15 | 15 | 15 | 15 |
| 5. Magnesium stearate | 1 | 1 | 1 | 1 | 1 | 1 | 2 | 3 |
| | 250 mg | 250 mg | 300 mg | 300 mg | 300 mg | 245 mg | 445 mg | 563 mg |

Procedure:
1. Mix Items 1-3 in a suitable mixer.
2. Add talc and magnesium stearate and mix for a short period of time.
3. Encapsulate on an appropriate encapsulation machine.

We claim:
1. A compound of the formula

$R_1$ is halogen or trifluoromethyl, m is 2, and n and s each is 1.

11. A compound in accordance with claim 1, (S)-1-(1-methylethylamino)-3-[4-[2-[4-[3-(2-chloro-10H-phenothiazin-10-yl)propyl]piperazine-1-yl]ethoxy]phenoxy]-2-propanol.

12. A compound in accordance with claim 1, N-[4-[2-[4- 3-(2-chloro-10H-phenothiazin-10-yl)propyl]-1-piperazinyl]ethoxy]phenyl]-α-methylethanamine.

13. A compound in accordance with claim 1, (R)-1-(1-methylethylamino)-3-[4-[2-[4-[3-(2-chloro-10H-phenothiazin-10-yl)propyl]piperazin-1-yl]ethoxy]-phenoxy]-2-propanol.

14. A compound in accordance with claim 1, (S)-1-(1-methylethylamino)-3-[4-[2-[4-[3-(2-trifluoromethyl)-10H-phenothiazin-10-yl)propyl]piperazin-1-yl]ethoxy]-phenoxy]-2-propanol.

15. A compound in accordance with claim 1, 1-[3-(2-chloro-10H-phenothiazin-10-yl)propyl]-4-[2-[4-[2-(1-methylethyl)aminoethoxy]phenoxy]ethyl]piperazine trihydrochloride.

* * * * *